US008601611B2

(12) United States Patent
Gogotsi et al.

(10) Patent No.: US 8,601,611 B2
(45) Date of Patent: Dec. 3, 2013

(54) METHODS OF PREPARING NANOPROBES AND ENDOSCOPE-LIKE DEVICES

(71) Applicant: Drexel University, Philadelphia, PA (US)

(72) Inventors: Yury Gogotsi, Warminster, PA (US); Gennady Friedman, Richboro, PA (US); Riju Singhal, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 13/645,561

(22) Filed: Oct. 5, 2012

(65) Prior Publication Data

US 2013/0091607 A1    Apr. 11, 2013

Related U.S. Application Data

(60) Provisional application No. 61/543,453, filed on Oct. 5, 2011.

(51) Int. Cl.
*B82Y 40/00* (2011.01)
*B82Y 5/00* (2011.01)

(52) U.S. Cl.
USPC ............. 850/60; 977/840; 977/742; 977/938; 850/32; 850/14

(58) Field of Classification Search
USPC ................. 850/60, 32, 14; 977/840, 742, 938
See application file for complete search history.

(56) References Cited

U.S. PATENT DOCUMENTS

| 7,824,620 | B2 | 11/2010 | Bau et al. | |
| 7,870,616 | B2 | 1/2011 | Meister et al. | |
| 8,119,021 | B2 * | 2/2012 | Gogotsi et al. | 252/62.51 R |
| 2003/0198956 | A1 * | 10/2003 | Makowski et al. | 435/6 |
| 2005/0208304 | A1 * | 9/2005 | Collier et al. | 428/403 |
| 2012/0121683 | A1 * | 5/2012 | Gogotsi et al. | 424/426 |

OTHER PUBLICATIONS

Freedman et al., "Magnetically assembled carbon nanotube tipped pipettes," Applied Physics Letters, Mar. 2007, 90(10), 103108, 1-3.
Jiang et al., "Selective Attachment of Gold Nanoparticles to Nitrogen-Doped Carbon Nanotubes," Nano Letters, Mar. 2003, 3(3), 275-277.
Korneva, G. et al., "Carbon nanotubes loaded with magnetic particles," Nano Letters, May 2005, 5(5), 879-884.
Mattia, D. et al., "Effect of graphitization on the wettability and electrical conductivity of CVD-carbon nanotubes and films," Journal of Physical Chemistry B, May 2006, 110(20), 9850-9855.
Mattia, D. et al., "Multifunctional carbon nanotubes with nanoparticles embedded in their walls," Nanotechnology, Apr. 2007, 18(15), 155305, 1-7.
Sharma et al., "Nanotoxicity Assessment toward the Applications of Carbon Nanotubes as a Small Biomolecule Carrier in Drug Delivery Systems," Nanotechnology, 2009, vol. 2, 150-153.
Singhal, R. et al., "Multifunctional carbon-nanotube cellular endoscopes," Nature Nanotechnology, Published Online on Dec. 2010, 6(1), 57-64.

(Continued)

*Primary Examiner* — Nikita Wells
(74) *Attorney, Agent, or Firm* — Woodcock Washburn, LLP

(57) ABSTRACT

The present invention is directed to methods of preparing nanoprobes, including multifunctional cellular endoscope-like devices, comprising nanotubes, nanorods, and/or nanowires.

17 Claims, 4 Drawing Sheets

(56) References Cited

OTHER PUBLICATIONS

Singhal, R. et al., "Multifunctional carbon-nanotube cellular endoscopes," Nature Nanotechnology, Supplementary Information, Published Online on Dec. 2010, 6(1), 1-14.

Singhal, R. et al., "Small diameter carbon nanopipettes," Nanotechnology, Jan. 2010, 21(1), 015304, 1-9.

* cited by examiner

METHODS OF PREPARING NANOPROBES AND ENDOSCOPE-LIKE DEVICES

CROSS REFERENCE TO RELATED APPLICATIONS

The present application claims priority to U.S. Patent Application No. 61/543,453, filed Oct. 5, 2011, which is incorporated by reference herein in its entirety.

GOVERNMENT RIGHTS

The subject matter disclosed herein was made with government support under Nanoscale Interdisciplinary Research Teams Grant CTS-0609062 awarded by the National Science Foundation. The Government has certain rights in the herein disclosed subject matter.

TECHNICAL FIELD

The present invention is directed to methods of preparing nanoprobes, including multifunctional cellular endoscope-like devices comprising nanotubes, nanorods, and/or nanowires.

BACKGROUND

Nanoscale devices for controlled fluid handling and cell interrogation have attracted a great deal of interest recently. Microfluidics led to major advances in biology and medicine, permitting DNA sequencing and breakthroughs in medical diagnostics. Further progress will require a million- to billion-fold reduction in the volume of fluid samples to the level of attoliters, which will enable probing of individual cells and intracellular organelles. On a single-cell level, glass micropipettes are employed for cellular injection and recovery applications ranging from therapeutic cloning to pharmacology. Difficulties, such as membrane rupture, inaccurate transplant, and fatal damage of crucial organelles, are often encountered using these capillaries to study single cells. Sharpened tubules formed by quartz capillary pulling, usually called "nanopipettes", can be drawn to ca. 25 nm. However, they bend and break easily. Therefore, the size is limited for practical reasons, and glass pipettes with tip diameters less than 500 nm are rarely used in practice. Targeting of the nucleus in fairly large cells (e.g. oocytes) is possible with glass pipettes, but specific organelles cannot be injected into or analyzed using the current technology.

Carbon nanotubes may also be used to interrogate or deliver payloads to cells. Such probes appear to offer significant advantages over sharpened glass micropipettes. But present methods of producing probes based on such nanotubes are limited.

SUMMARY

The present invention is directed to methods of preparing nanoprobes, including multifunctional endoscope-like devices, comprising nanotubes, nanorods, and/or nanowires, for use in probing cells.

Certain embodiments of the present invention provide methods of preparing nanoprobes, each having a handle with an at least partially hollow distal chamber in fluid communication with a distal tip and at least one nanoelement protruding therefrom; each method comprising: (a) placing at least one nanoelement suspended in a solvent into the distal chamber; (b) contacting the distal tip with a surface wettable by the solvent for a time and under conditions effective for at least one nanoelement to contact said surface while remaining at least partially within the distal chamber; (c) withdrawing the distal tip of the nanoprobe away from the surface while maintaining contact of the at least one nanoelement with said surface until solvent in the distal tip is no longer in contact with said surface.

In other embodiments, the methods comprise: (a) placing a plurality of nanoelements suspended in a solvent into the distal chamber; (b) contacting the distal tip with a surface wettable by the solvent for a time and under conditions effective for a single nanoelement to contact said surface while remaining at least partially within the distal tip; (c) withdrawing the distal tip of the nanoprobe away from the surface while maintaining contact of the single nanoelement with said surface until solvent in the distal tip is no longer in contact with said surface.

In some embodiments, methods further comprise holding the nanoprobe at the distance from the surface for a time and under conditions sufficient to allow at least a portion, and preferably all, of the solvent remaining in the distal tip to evaporate.

In still further embodiments, some methods further comprise sealing the distal tip to form a leak-resistant seal between the nanoelement and the distal tip.

BRIEF DESCRIPTION OF THE DRAWINGS

The inventors have discovered a novel method of preparing nanoprobes capable of interrogating and delivering payload materials into cells.

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In addition, the drawings are not necessarily drawn to scale. In the drawings:

FIG. 1(d) is a TEM micrograph of a tube wall. Annealing in vacuum at 1500-1800° C. eliminated disorder and led to graphitization of tube walls. Scale bar=5 nm Chemical vapor deposition growth in pores of alumina templates allowed control of carbon nanotube diameters from 300 nm down to 10 nm, wall thickness ranging from 5 nm to 60 nm, and carbon nanotube lengths up to several hundred microns. Tubes were straight and typically open at both ends. They were transparent to both visible light and electron beam.

FIG. 2(a) is a schematic of the assembly steps: (i) pipette in contact with glass substrate surface, (ii) pipette retracted, exposing the carbon nanotube, (iii) nanotube-pipette junction sealed with epoxy. FIG. 2(b) is an optical micrograph of a nanotube released from the template and assembled at the pipette tip. FIG. 2(c) is an optical micrograph of an assembled pipette sealed with epoxy resin. Scale bar in FIGS. 2(b)-(c)=10 µm.

FIG. 3(a) provides a general view. Scale bar=15 µm. In FIG. 3(b), epoxy glue provides sealing of the glass pipette entry, while the tip of the endoscope remains open and allows fluid transfer (FIG. 3(c)). The tube wall thickness was kept at about 10% of the outer diameter. Scale bar in FIG. 3(b)=1 nm, in FIG. 3(c)=100 nm.

FIGS. 5(a)-(b) show differential interference contrast micrographs showing a 100 nm nanotube tip of the endoscope bending (left) and elastically recovering its shape (right) when pushed against a cell membrane (FIG. 5(a)) or a glass slide (FIG. 5(b)). FIG. 5(c) shows sequential optical micrographs of a nanotube tip bending towards a magnetic field (white arrow). Superparamagnetic properties and flexibility of the nanotube tip allow remote magnetic manipulation

DETAILED DESCRIPTION OF ILLUSTRATIVE EMBODIMENTS

Figure 1:
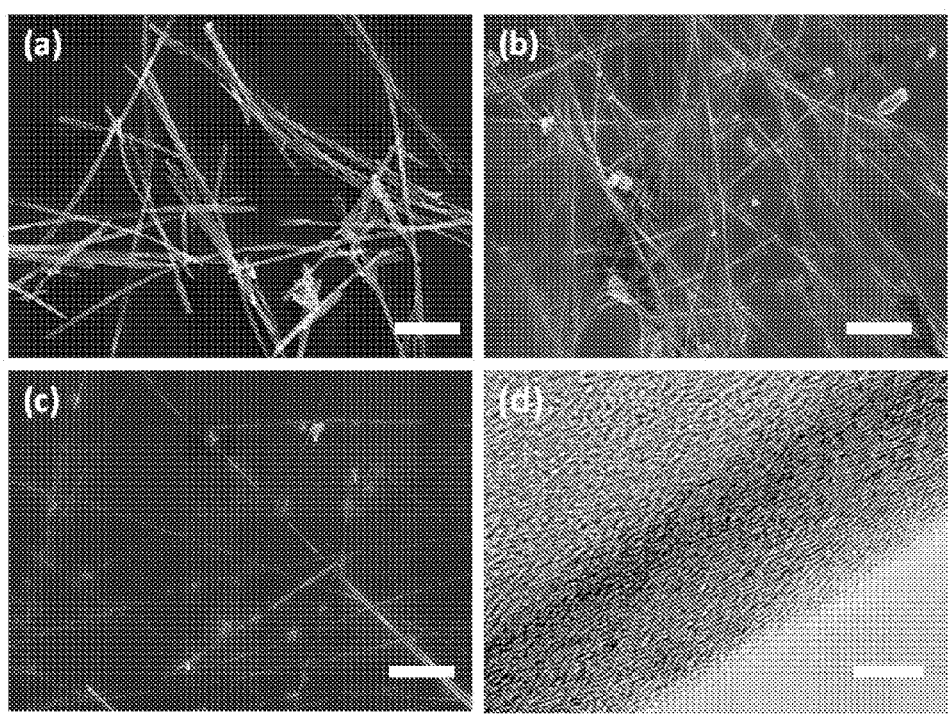
FIG. 1 show micrographs of the structure of some nanotubes prepared by chemical vapor deposition used for endoscope tips. Scanning electron micrographs of 200 nm (FIG. 1(a)), 100 nm (FIG. 1(b)), and 50 nm (FIG. 1(c)) nanotubes (average outer diameters) released from the alumina template. Scale bar in FIGS. 1(a)-(c)=5 µm.

The present invention may be understood more readily by reference to the following description taken in connection with the accompanying Figures and Examples, all of which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer both to the features and methods of making and using nanoprobes, as well as the nanoprobes themselves.

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Finally, while an embodiment may be described as part of a series of steps or part of a more general structure, each said step may also be considered an independent embodiment in itself.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are described herein.

The present invention(s) are directed to methods of preparing nanoprobes, including nanoprobes that may function as cellular endoscopes. Various embodiments, then, include those methods of preparing nanoprobes, each having a handle with an at least partially hollow distal chamber in fluid communication with a distal tip and at least one nanoelement protruding therefrom; each method comprising: (a) placing at least one nanoelement suspended in a solvent into the distal chamber; (b) contacting the distal tip with a surface wettable by the solvent for a time and under conditions effective for at least one nanoelement to contact said surface while remaining at least partially within the distal chamber; (c) withdrawing the distal tip of the nanoprobe away from the surface while maintaining contact of the at least one nanoelement with said surface until solvent in the distal tip is no longer in contact with said surface.

In other embodiments, the methods comprises: (a) placing a plurality of nanoelements suspended in a solvent into the distal chamber; (b) contacting the distal tip with a surface wettable by the solvent for a time and under conditions effective for a single nanoelement to contact said surface while remaining at least partially within the distal tip; (c) withdrawing the distal tip of the nanoprobe away from the surface while maintaining contact of the single nanoelement with said surface until solvent in the distal tip is no longer in contact with said surface.

In some embodiments, methods further comprise holding the nanoprobe at the distance from the surface for a time and under conditions sufficient to allow at least a portion, and preferably all, of the solvent remaining in the distal tip to evaporate.

In still further embodiments, some methods further comprise sealing the distal tip to form a leak-resistant seal between the nanoelement and the distal tip; i.e., over the tip and around the nanoelement, so that the nanoelement penetrates through the seal. This may be accomplished by applying a sealant to the distal tip (i.e., covering the open end of the distal tip and surrounding a portion of the diameter of the nanoelement) and curing said sealant. The sealant may be a thermal or photopolymerizable sealant, such as are known in the art. Epoxies are preferred, in part, for their convenience of use. Where the sealant is a photopolymerizable sealant, the sealing step may comprise applying light—typically ultraviolet light—the nature of the light depending on the character of the sealant. This sealing provides an adherent bond between nanoelement and distal tip and provides structural integrity to the nanoprobe.

Without necessarily intending to be bound by correctness or incorrectness of any such suggested mechanism or mode of action, it appears that the wettable surface provides a wicking action for the solvent which generates a fluid flow through the distal tip, thereby providing a convective flow through the distal chamber of the nanoprobe. This convective flow drags the nanoelements to the distal tip while aligning them in the direction of the convective flow. See, e.g., FIG. 2.

Figure 2:
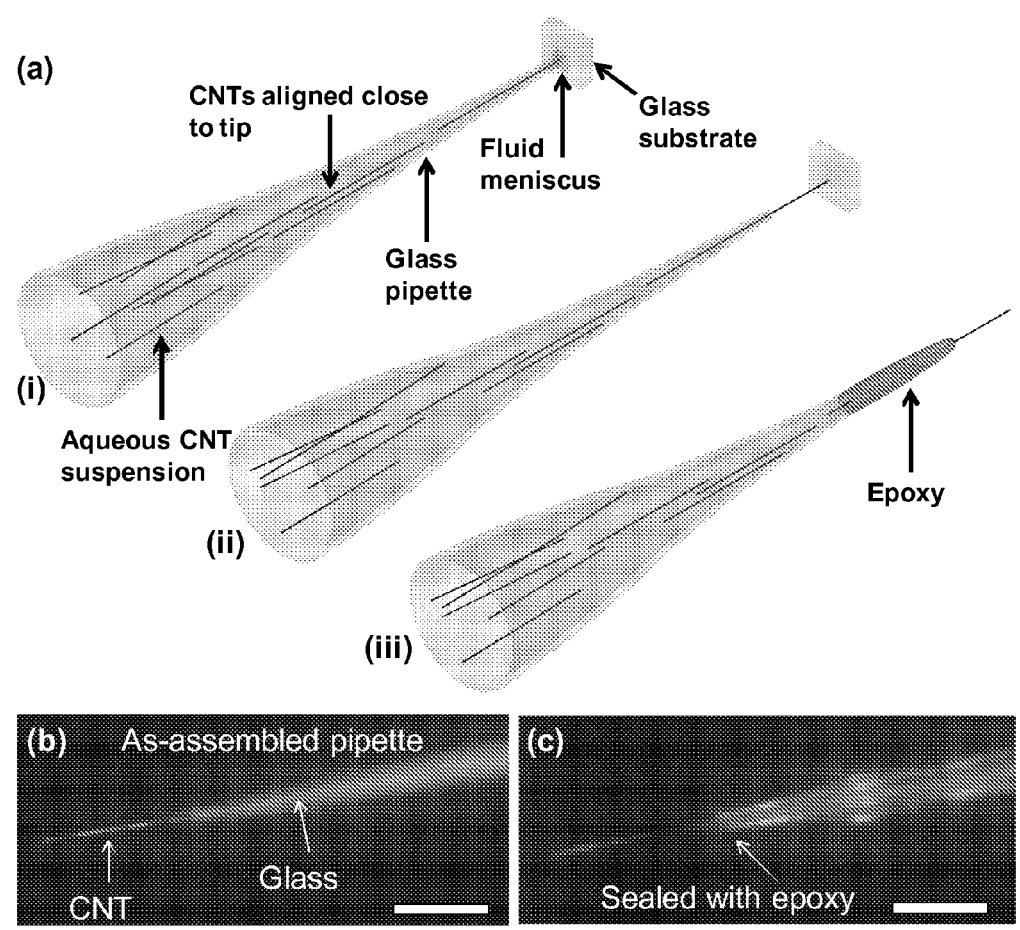
FIG. 2 provides a schematic representation of one embodiment of the assembly and sealing of cellular endoscopes.

The nanoprobe handles (having an at least partially hollow distal chamber in fluid communication with a distal tip—see, e.g., FIG. 2) may comprise virtually any material, but glass—e.g., silicate or borosilicate glass—appears to be a preferred material for this purpose, allowing for the simple preparation of such handles by heating and drawing readily available micropipettes (e.g., Example 2). For example, simple handles may be prepared by using a pipette puller to make glass pipettes in which the inner cross-sectional dimension (e.g., diameter, where the opening is circular) of the distal tips are in a range of about 0.1 micron (100 nm) to about 0.1 mm (1000 micron). Other embodiments provide that the inner cross-sectional dimension of the distal tips are in a range of about 100 nm to about 1000 nm or in a range of about 400 nm to about 900 nm (i.e., about 0.4 microns to about 0.9 microns) (FIG. 2(a)). For example, pipettes of borosilicate glass can be prepared by pulling commercially available capillaries (BF100-78-7.5, Sutter Instruments) in a laser based pipette puller (P2000, Sutter Instruments). Such devices may contain a distal chamber having a volume in the nanoliter to microliter range—i.e., about 1 nanoliters to about 0.1 to 100 microliters—or even milliliter range.

Nanoprobes may also be made wherein the glass [micropipette] handles have an electrically conductive coating (e.g., a metallic or conducting carbon coating) on the internal surfaces of the distal chambers/distal tips, thereby providing for an electrical connection between the nanoelement and the carbon layer. Using such a conducting tip of the endoscope with electrical connections opens up the possibility of many applications, and such capabilities of electrical testing in cellular environments can be combined with magnetic manipulation, fluid delivery and sampling As used herein, the term nanoelements includes nanotubes, nanorods, or nanowires; i.e., structures whose outer diameters range from about 1 nm to about 500 nm. In independent embodiments, the diameters of these structures may be in a range bounded at the lower end by a value of about 1 nm, about 2 nm, about 3 nm, about 4 nm, about 5 nm, about 10 nm, about 20 nm, about 30 nm, about 40 nm, or about 50 nm and independently bounded at the upper end by a value of about 500 nm, about 250 nm, about 200 nm, about 150 nm, about 100 nm, about 50 nm, or about 25 nm. Exemplary, non-limiting ranges include those from about 2 nm to about 100 nm, about 5 nm to about 250 nm, about 10 nm to about 250 nm, about 10 nm to about 100 nm, or about 50 to about 400 nm, or about 200 nm to about 350 nm. Using certain methods (e.g., template methods), carbon nanotubes may be produced in which the outer diameters are substantially the same—for example, 50 nm, 100 nm, or 200 nm (e.g., with corresponding inner diameters of 30 nm, 60 nm, and 150 nm).

In various embodiments where the nanoelements comprise lumens—i.e., nanotubes—the nanotubes may be single or multiwall nanotubes. In certain of these embodiments, the wall thickness of the nanotubes are in the range bounded at the lower end by a value of about 2 nm, about 3 nm, about 4 nm, or about 5 nm and independently bounded at the upper end by a value of about to about 75 nm, about 50 nm, about 40 nm, about 30 nm, about 25 nm, about 20 nm, or about 10 nm. Exemplary, non-limiting wall thicknesses may be in a range of about 2 nm to about 50 nm or about 10 nm to about 25 nm.

In independent embodiments, these nanoelements (including nanotubes, nanorods, and nanowires) have lengths in a range of about 10 microns to about 400 microns, about 20 microns to about 200 microns, about 25 microns to about 200 microns, or about 50 microns to about 60 microns.

These nanoelements may comprise carbon and/or inorganic (i.e., non-carbonaceous) materials—for example, including carbon nanotubes (single or multiwall), and/or nanotubes comprising carbon-boron, carbon-nitrogen, molybdenum sulfide, tin(IV) sulfide, titania, tungsten sulfide, zirconia, or a transition metal/chalcogen/halogenide Nanorods or nanowires may also comprise metals (e.g., Ni, Pd, Pt, Au), and/or semiconducting (e.g., Si, InP, GaN, etc.), and insulating (e.g., SiC, $SiO_2$, $TiO_2$) materials.

Figure 5:
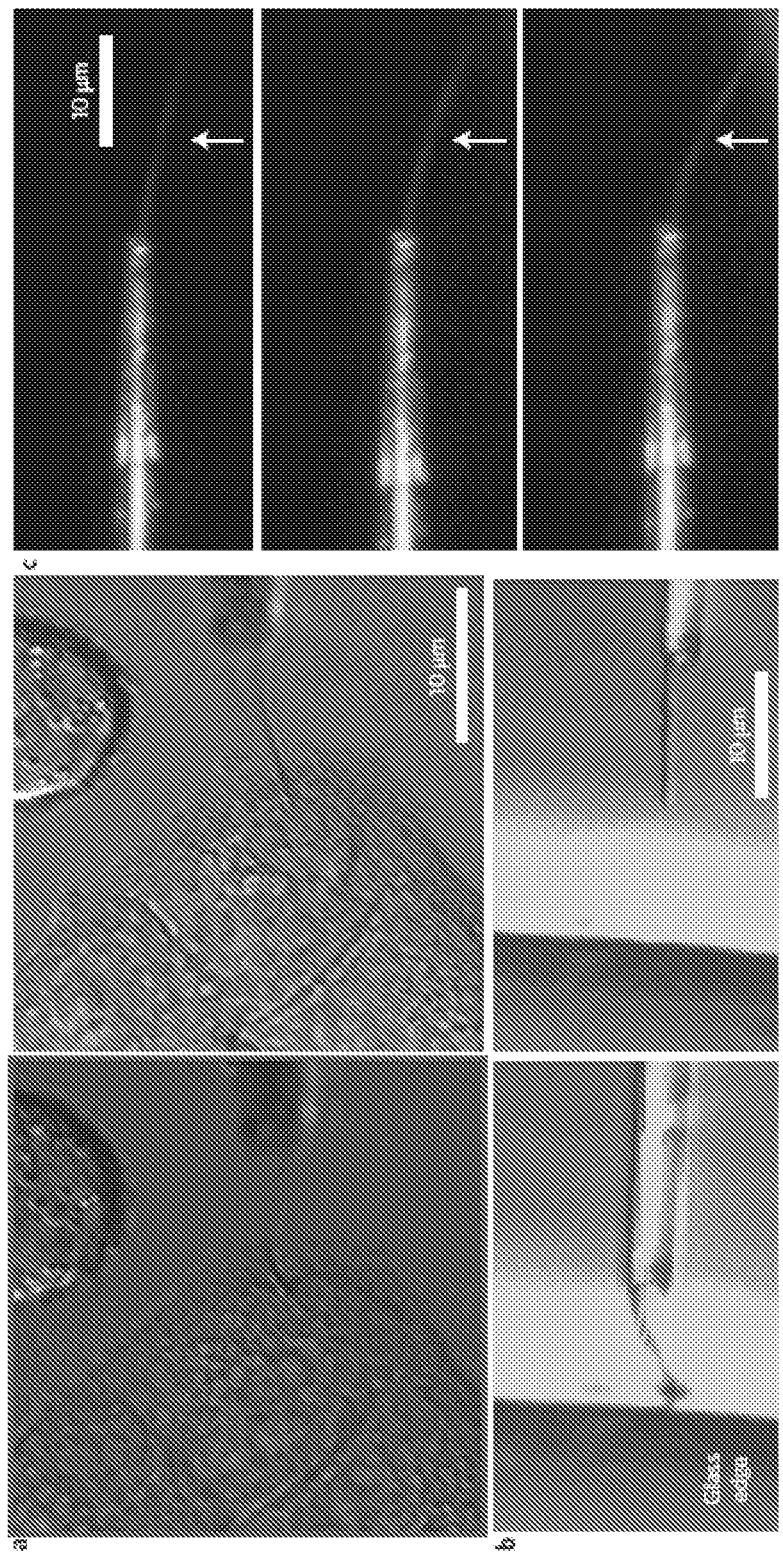
FIG. 5 illustrates the mechanical robustness, flexibility and remote manipulation of the nanotube endoscope.

In certain preferred embodiments, the nanoelements comprise carbon nanotubes, either in part or entirely, based on the total population of the nanoelements. These nanotubes may comprise carbon, boron-carbon or carbon-nitrogen nanotubes, and may be single- or multi-walled nanotubes. In other independent embodiments, the carbon nanotubes comprise amorphous or graphitic carbon. Carbon nanotubes (CNT) offer advantages of mechanical robustness, rigidity at diameters down to ca. 10 nm and electrical conductivity. See, e.g., FIG. 5. Cylindrical shape, tunable diameter, and biocompatibility of carbon make carbon nanotubes especially suitable for cellular probing. Because of the small dimensions of carbon nanotubes, the cell membrane penetration force is dramatically reduced.

These nanoelements, including nanotubes, may be prepared by any conventional method, including physical or chemical vapor deposition methods, either catalytically or non-catalytically. For example, they may be prepared in bulk or vertically oriented (and later separated) from a catalyzed platform substrate, and/or by using anodized alumina template methods. The use of anodically oxidized alumina templates is attractive in allowing for the incorporation of additives on either the inside or outside surfaces of the nanotubes (see, e.g., Example 1). In addition, the nanoelements may be functionalized either before or after incorporation into the nanoprobes, again using methods known to those skilled in the art (see, e.g., Examples 1, 4, and 5). For example, nanotubes (including carbon nanotubes) useful for the inventive methods include those filled with fluorescent nanoparticles or coated with fluorescent dyes; or coated with gold nanoparticles; or filled with magnetic or non-magnetic (including pharmaceutically active) materials; exemplary material includes gold. In separate embodiments, the nanoelements comprise magnetic or non-magnetic carbon nanotubes, prepared by the inclusion of magnetic dopants or fill particles. For example, the magnetic character may be introduced by incorporating magnetic, paramagnetic, ferromagnetic, or superparamagnetic materials into the internal or external surfaces of the nanotubes, or by incorporating such materials within the walls or the lumen of the nanotubes.

By filling the nanotubes with superparamagnetic nanoparticles, magnetic tips can be and have been produced. This allows that, when the endoscope tip is brought close to the surface of a permanent magnet, the nanotube deflects in response to the magnetic force (FIG. 5(c)). Based on the magnetic moments of these carbon nanotubes ($1 \times 10^{-16}$ to $1 \times 10^{-15}$ A m$^2$), estimates indicate that the nanotube tip of an endoscope (diameter, 100 nm; length, 60 μm) would deflect 5-10 μm at an external field strength of ca. 0.5 T. With these estimates, electromagnets or permanent magnets can be used to generate submicrometer deflections for precise positioning of the tip inside the cell. Such deflections would be difficult or impossible to achieve with conical pipettes, for which the diameter increases at least to micrometer dimensions over a length of 10 μm or so.

Where the nanotubes are magnetic or metallic, methods of preparing the nanoprobes may be conducted in the presence or absence of an applied magnetic field. That is, the inventive methods described herein do not require the interaction of a magnetic or metallic nanoelement with an externally applied electric or magnetic field in order to operate effectively.

As described above, methods of preparing the nanoprobes include those embodiments where a single nanoelement is suspended within a solvent and drawn out the distal tip; where a plurality of nanoelements are suspended within a solvent and some portion of those nanoelements are drawn out the distal tip; and where a plurality of nanoelements are suspended within a solvent and a single nanoelement is drawn out the distal tip. In preferred embodiments, a plurality of nanoelements (preferably carbon nanotubes) is suspended within a solvent and a single nanoelement is drawn out the distal tip. While the concentration of the nanoelements suspended in the solvent is not critical, separate embodiments provide that this concentration be less than about 5 wt %, less than about 2 wt %, less than about 1 wt %, less than about 0.5 wt %, or less than about 0.25 wt %, relative to the combined weight of the nanotubes and the solvent. In an exemplary embodiment, a concentration of about 0.1 wt % nanotubes in water was found to provide a convenient amount of material for the method.

Generally, during the preparation procedure, the handles (comprising the distal chambers) are positioned horizontally and injected with a nanoelement suspensions from the large bore end—using a syringe—before the distal tip of the micropipette is brought in contact with a solvent-wettable substrate. The movement of the nanoelements through the distal chamber is most simply monitored optically—e.g., by way of an optical microscope—until the first nanotube contacts the surface of the substrate. CNTs with about 50 nm, 100 nm and 200 nm outer diameters (with corresponding inner diameters of ca. 30, ca. 60 and ca. 150 nm, respectively) and 10-20 μm length extending beyond the glass are conveniently visible using optical microscopy. Carbon nanotubes with outer diameters ranging from 50 to 200 nm and lengths of tens of micrometers can be conveniently be visualized during optical microscope-based cell experiments. These nanoscopic dimensions provide sufficient mechanical strength to penetrate the membrane of the cell unnoticed, then manoeuver through the intracellular environment without inducing stress. According to the inventors' estimates, endoscopes with nanoelement diameters of ca. 100 nm should pierce the membrane at normal forces of tens of nanonewtons. Thus, endoscopes with aspect ratios of over 100 could be capable of penetrating deep into a cell without buckling. Indeed, a nanotube with an outer diameter of 100 nm and inner diameter of 70 nm (effective tip area of ca. 4,000 nm$^2$) requires a force of 40 nN to overcome a membrane with a lytic stress of 10 MPa. Buckling was observed in FIG. 5(a) as a result of the carbon-nanotube tip touching the glass plate surface, and the endoscope safely survived the repetitive deformation. Other monitoring methods may also be used, including light detection or (in the case of magnetically coated nanotubes) electrical detectors. The smallest tube tips can be better observed if filled with fluorescent nanoparticles or when a fluorescent dye is attached to their surface.

Once the first nanoelement (or otherwise desired number of nanoelements) contacts the substrate surface, the distal tip of the nanoprobe is withdrawn from the surface, the attractive forces between the nanotube and the surface being sufficient to hold the nanotube to the surface. The distal tip of the nanoprobe is withdrawn from the surface while maintaining contact of the single nanoelement with said surface until solvent in the distal tip is no longer in contact with said surface. For stability, the nanoelement is only drawn out to a fraction of its length, ranging from about 20% to about 80%, about 30% to 70%, or about 40% to 60% of the total length. Then, at least a portion, and preferably all, of the solvent is allowed to evaporate, after which the attractive forces between nanoelement and inner surface of the distal chamber/tip are sufficiently strong to hold the nanoelement in place. An adhesive is then typically applied and cured, affixing the nanoelement in position and forming a leak resistant seal at the distal tip of the nanoprobe.

The methods may be operated wherein the solvent comprises water or alcohol (e.g., ethanol and/or isopropanol), or a mixture thereof. Solvent systems comprising water, including water itself, appear to be a preferred. Again, without intending to be necessarily bound to the correctness or incorrectness of any such suggested mechanism or mode of action, it appears that water is better able to drag the nanotubes through the distal chamber to the distal tip during its convective flow than are alcohols, either by virtue of its higher viscosity or possibly its intermolecular attractiveness to the surface of the nanoelements, especially carbon nanotubes. Water is additionally attractive in that it does not dissolve or interfere with the curing of some of the adhesives considered useful in the preparation of certain of the nanoprobes (e.g., epoxies, see below). In fact, if alcohols are used as the initial solvent for the movement of the nanoelements to the distal tips of the nanoprobes, it may be useful to allow them to evaporate, refill the distal tip with water, and then seal the ends of the nanoprobes, so as to prevent entry of excessive epoxy, for example, into the distal chamber.

The methods have each been described in terms of "contacting the distal tip with a surface wettable by the solvent for a time and under conditions effective for at least one nanoelement to contact said surface." While not necessarily limiting in terms of any particular composition, any surface able to fulfill this functional criterion—i.e., wicking organic polymers or inorganic surfaces—may be used. In certain embodiments, such a surface comprises sintered ceramic or glass oxides. In preferred embodiments, such surfaces comprise an oxide of aluminum, silicon, or both aluminum and silicon. Physical features, such as micro- or nano-pores may also be incorporated into the surface to enhance this wicking effect. For example, porous anodic aluminum oxide may be preferred. Such surfaces may enhance wicking/wetting by the capillary filling of cylindrical pores.

EXAMPLES

The following examples, while illustrative individual embodiment, are not intended to limit the scope of the described invention, and the reader should not interpret them in this way.

Example 1

Nanotube Tip Fabrication

Alumina membranes of specific pore sizes varying from 50 nm to 200 nm and thicknesses from 60 to 100 nm were synthesized by anodization of aluminum foils. Carbon was deposited on the walls of these pores by performing chemical vapor deposition (CVD) on these membranes at 670° C., using ethylene as the feedstock gas for different time periods depending on the pore size, as described in Mattia, D. et al., "Effect of graphitization on the wettability and electrical conductivity of CVD-carbon nanotubes and films," *Journal of Physical Chemistry B* 110, 9850-9855 (2006), which is incorporated by reference herein in its entirety. Typically, this lasted 6 hrs for a 200 nm (pore size) membrane, 2.5 hrs for a 100 nm membrane and 1 hr for a 50 nm membrane. The carbon nanotubes were released by dissolving the alumina template in 1 M NaOH. See, e.g., D. Mattia, et al., "Embedding Nanoparticles in the Walls of Carbon Nanotubes," *Nanotechnology* 18, 155305 (2007), which is incorporated by reference herein in its entirety. Exemplary micrographs of the CVD nanotubes used in this study are shown in FIG. 1.

For magnetic CNTs, the alumina membranes after CVD were soaked in a solution of organic ferro-fluid (EMG 911, Ferrotech Corporation), which carries magnetite particles (D~10-15 nm), and were left to dry. This process resulted in deposition of a thin layer of superparamagnetic $Fe_3O_4$ particles on the inner walls of the CNTs, such as described in Korneva, G. et al., "Carbon nanotubes loaded with magnetic particles," *Nano Letters* 5, 879-884 (2005), which is incorporated by reference herein in its entirety. Magnetic carbon nanotubes were then released from the alumina membrane by dissolution in 1M NaOH solution at 90° C. for 3 hrs. The nanotubes were recovered by filtration and neutralized by washing with de-ionized water. The nanotubes were suspended in iso-propanol or water for the assembly process.

Example 2

Pipette Fabrication

Pipettes of borosilicate glass were prepared by pulling commercially available capillaries (BF100-78-7.5, Sutter Instruments) in a laser based pipette puller (P2000, Sutter Instruments). Glass pipettes were prepared with inner diameters of ~100-1000 nm (FIG. 2(*a*)).

For CNTs to be used for electrochemical measurements, quartz pipettes were coated with carbon on the inside, prepared according to Singhal, R., et al., "Small diameter carbon nanopipettes," *Nanotechnology* 21, 015304 (2010), which is incorporated by reference herein in its entirety. These were filled with ethanolic CNT suspensions, and the assembly process remained the same as described below, except that the sealing was performed in two stages. First silver epoxy (Chemworks, CW2400) was applied at the junction to provide a permanent electrically conductive path from the nanotube to the carbon layer. Next, regular (non-conducting) epoxy was used to completely coat the existing silver epoxy so that the only conductive surface in solution is the CNT.

Example 3

Flow-driven Assembly

CNTs were assembled into pipette tips using flow driven assembly (FIG. 2(*a*)). The aqueous (or ethanolic) dispersion of CNTs was injected into the back-end of the pipette with a syringe. The pipette was mounted horizontally on a nanomanipulator with the tip positioned 10-50 μm from the surface of a glass slide. A drop of water was placed between the pipette outlet and the glass slide. The pipette tip was brought in contact with the substrate and the liquid from the pipette was allowed to flow out. Once a nanotube reached the glass slide, the pipette was retracted to release 10-30 μm of the tube and left to dry. At that time, the liquid bridge and the droplet were allowed to evaporate leaving a single nanotube protruding from the pipette tip. This method allowed the manufacture of endoscopes with any kind of tubes starting from ~50 nm in diameters (limited by the resolution of the optical system). The method can also be scaled up by using dielectrophoresis. This may be done by using a glass pipette coated with a conducting material (e.g., Pt or C), facing it to the sharp edge of a conducting substrate (e.g., a metal or metal coated substrate), connecting the pipette and the substrate to two electrodes of a voltage source, and applying a suitable alternating potential between the pipette and the substrate edge. In the latter case, no observation of the nanotubes is required and tips of very small diameters can be produced.

Figure 3:
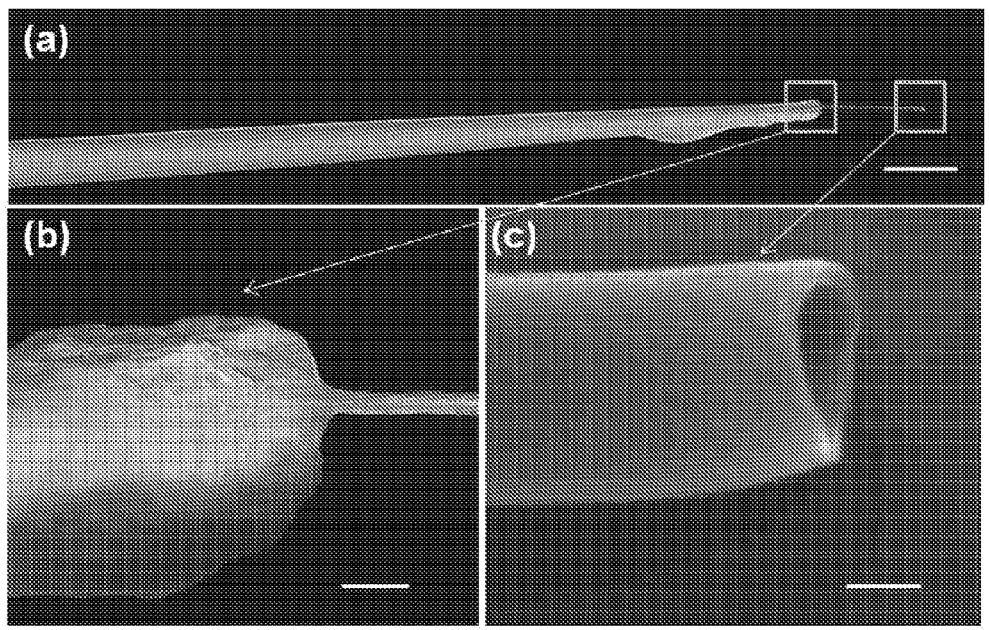
FIG. 3 includes SEM images of an assembled nanotube tipped cellular endoscope with a ca. 300 nm outer diameter of the tip.

The nanotube protruding from the dried pipette tip was then secured by sealing the gap between the nanotube and the glass with a commercially available epoxy (Elmer's Products Inc.). For this purpose, another glass pipette was loaded with the epoxy and brought (under optical microscope) in contact with the nanotube-pipette junction until a small drop of epoxy was transferred, which then sealed the glass tip opening (FIG. 2(*c*)). Tips of any required diameters, both larger and smaller than the ones reported in this study, can be inserted into glass pipettes, which can also be produced in a variety of shapes and sizes. An example of a larger (~300 nm outer diameter) tip is shown in FIG. 3. Larger and sturdier tips can be used for nanoscale analytical chemistry, forensic and electrochemistry studies, or for interrogating large cells and plant cells with stiff cell walls. The conductivity, contact angle and mechanical properties of nanotubes tips can be controlled by annealing and surface treatments.

Example 4

Figure 4:
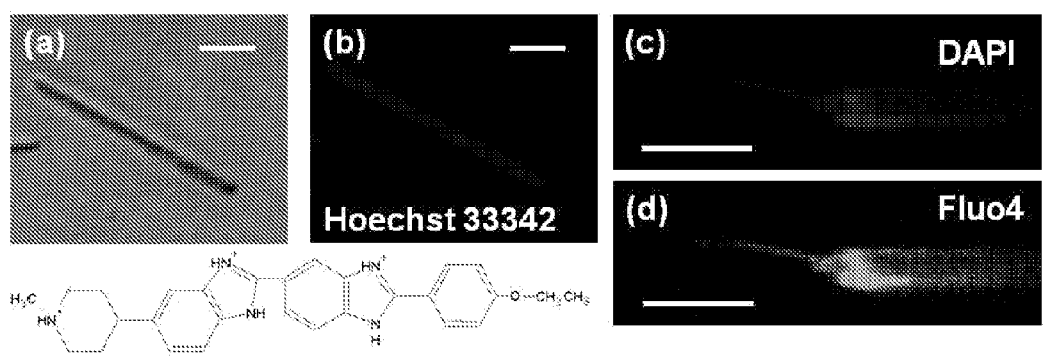
FIG. 4 Differential interference contrast (FIG. 4 (a)) and fluorescent (FIG. 4 (b)) images of a 200-nm CNT labeled with Hoechst 33342 dye, the structural formula of which is shown under the micrographs. (c, d) show an assembled endoscope excited by two different (405 and 488 nm) lasers (z-stack images). Scale bar=10 μm.

Fluorescent Endoscope Tips

Where fluorescent endoscope tips were required, the CNTs were rendered fluorescent by covalent interaction of the surface functional groups and the fluorescent dye. The method of introducing the acyl chloride groups on the surfaces of carbon nanostructures is well known. CNTs (0.01 g) were treated with 35 mL of 10% v/v $HNO_3$:$H_2SO_4$ (4:1) for 48 h, subsequently filtered through the polyester nucleopore membrane (pore size of 0.2 nm; Osmonic Corp.), and washed to introduce the carboxylic groups on the surface of the CNTs (CNT-COON). The resultant functionalized CNTs were refluxed at 70° C. for 24 h with 60 mL of $SOCl_2$ (Sigma Aldrich) and 1 mL of anhydrous N,N dimethylformamide (DMF) (Sigma Aldrich), which acted as a catalyst for this reaction. The acyl chloride derivative (CNT-COCl) was washed with anhydrous tetrahydrofuran (THF) 3 times to remove excess thionyl chloride, dried at ambient temperature, and dispersed in ethanol. An aqueous solution of 1 mg/l mL Hoechst 33342 dye was added to the ethanolic suspension of the CNT-COCl and stirred for 72 h. The dye molecules were covalently linked to the CNT surface through the amide linkages formed by the reaction between the amine groups on the dye and the acyl groups on the CNTs. The CNT-dye suspension was filtered, washed and the functionalized CNTs (FIGS. 4(*a*)-(*b*)) were finally dispersed in ethanol to be used for assembly of the fluorescent endoscopes. The physically adsorbed dye was removed from the CNT surface by washing with ethanol. The modified tips showed bright fluorescence (FIG. 4(*b*)), which was retained after penetrating the cell membrane and after removing the endoscope from an HeLa cell.

Physisorption of a fluorescent dye on the pipette tip, by dipping an assembled CNT, with the surface functionalized with carboxyl groups, into the aqueous dye solution, is an alternative way to make the tips visible in fluorescent images and to steer them more accurately to the desired location in the cell (FIG. 4(c)-(d))

Example 5

Embedding Gold in the Nanotubes

Gold colloids were produced via a wet-chemical method. Hydrogen tetrachloroaurate ($HAuCl_4$; 0.01-0.02 g) and 10 mL de-ionized (DI) water were mixed in a vial by magnetic stirring for 1 h. The aqueous solution was heated to ca. 100° C. (boiling) and then 3 mL of sodium citrate (0.02-0.13 g in powder) was added. When the solution became dark red in color (about 5 min), it was removed from the hot plate and kept under constant stirring for 2 h. After cooling, the colloid solution was refrigerated until use. The shape and size distribution of all colloids was determined by TEM. Gold nanoparticles (ca. 20 nm in diameter) were attached to template-grown CNTs using an electrostatic functionalization technique, using a technique described in K. Y. Jiang, et al., Nano Lett. 2003, 3, 275. Briefly, positively charged cationic polyelectrolyte was adsorbed onto acid-treated CNTs with negatively charged carboxyl and hydroxyl surface functional groups. Negatively charged gold nanoparticles were then adsorbed onto the outer surfaces of these positively charged CNTs. Adjusting the incubation time and nanoparticle concentration in the colloidal solution controlled the particle density. Nanotubes used for endoscope tips have already shown Raman activity after incorporation of Au nanoparticles and can be used as probe tips. The CNTs covered with Au nanoparticles were assembled onto glass tips, producing SERS-active cellular endoscopes.

Example 6

Flow Capability Through Endoscopes

To test the capacity of the endoscopes to deliver payloads, yellow fluorescent polypropylene particles (ca. 40 to 60 nm diameter; Spherotec Inc.) were suspended in DI water and 10 µL of this suspension was dispensed onto a cleaned glass coverslip. A dry, empty 100 nm endoscope was brought to the surface and dipped into the droplet using an Eppendorf manipulator. The movement of particles within the CNT of the assembled pipette was visualized using a 100× oil-immersion objective and FITC spectra (excitation/emission wavelengths 488/510 nm) on a FluoView™ FV1000 confocal microscope.

Example 7

Material Delivery Using Endoscopes

Fluorescent particles were transferred into Human osteosarcoma (HOS) cells using endoscopes. Cells were seeded at 200,000 cells/dish in a glass-bottom dish from MatTek 24 hours prior to imaging. Before imaging, cells were stained with Mitotracker Orange CMTMRos at a final concentration of 25 nM for 15 min and washed in growth media. The endoscope with 100 nm outer diameter tip and inner diameter just a bit larger than the particle was back-filled with a suspension of yellow fluorescent particles.

It is to be understood that while the invention has been described in conjunction with the preferred specific embodiments thereof, that the foregoing description and the examples that follow are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains. In addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document are hereby incorporated herein by reference, each in its entirety, for all purposes.

What is claimed:

1. A method of preparing a nanoprobe having a handle with an at least partially hollow distal chamber in fluid communication with a distal tip and at least one nanoelement protruding therefrom; said method comprising:
   (a) placing a plurality of nanoelements suspended in a solvent into the distal tip;
   (b) contacting the distal tip with a surface wettable by the solvent for a time and under conditions effective for a single nanoelement to contact said surface while remaining at least partially within the distal tip;
   (c) withdrawing the distal tip of the nanoprobe away from the surface while maintaining contact of the single nanoelement with said surface until solvent in the distal tip is no longer in contact with said surface.

2. The method of claim 1, further comprising holding the nanoprobe at the distance from the surface for a time and under conditions sufficient to allow at least a portion of the solvent remaining in the distal tip to evaporate.

3. The method of claim 1, further comprising sealing the distal tip to form a leak-resistant seal between the nanoelement and the distal tip.

4. The method of claim 1, wherein the at least one nanoelement is non-magnetic.

5. The method of claim 1, wherein at least a portion of the nanoelements comprise carbon.

6. The method of claim 5, wherein at least a portion of the nanoelements are carbon nanotubes.

7. The method of claim 5, wherein the single nanoelement comprises carbon.

8. The method of claim 7, wherein the single nanoelement is a carbon nanotube.

9. The method of claim 1, wherein the solvent comprises water, ethanol, isopropanol, or a mixture thereof.

10. The method of claim 1, wherein the solvent comprises water.

11. The method of claim 1, wherein the surface comprises an oxide of aluminum, silicon, or both aluminum and silicon.

12. The method of claim 1, wherein the surface comprises a sintered alumina.

13. The method of claim 1, wherein the handle with an at least partially hollow distal chamber in fluid communication with a distal tip comprises glass.

14. The method of claim 3, wherein the sealing comprises applying a sealant to the distal tip and curing said sealant.

15. The method of claim 14, wherein the sealant is a thermal or photo-polymerizable sealant.

16. The method of claim 15, wherein the sealant is an epoxy.

17. The method of claim 15, wherein the sealant polymerizes by applying ultraviolet light.

* * * * *